(12) United States Patent
Fano

(10) Patent No.: US 11,213,720 B2
(45) Date of Patent: Jan. 4, 2022

(54) POSTURE TRAINING DEVICE AND METHOD OF USING THE SAME

(71) Applicant: Smart Spine, LLC, Boca Raton, FL (US)

(72) Inventor: Darren Fano, Boca Raton, FL (US)

(73) Assignee: SMART SPINE, LLC, Boca Raton, FL (US)

( * ) Notice: Subject to any disclaimer, the term of this patent is extended or adjusted under 35 U.S.C. 154(b) by 777 days.

(21) Appl. No.: 15/499,144

(22) Filed: Apr. 27, 2017

(65) Prior Publication Data
US 2017/0312569 A1    Nov. 2, 2017

Related U.S. Application Data

(60) Provisional application No. 62/328,463, filed on Apr. 27, 2016.

(51) Int. Cl.
| A61F 5/02 | (2006.01) |
| A63B 23/02 | (2006.01) |
| G09B 19/00 | (2006.01) |
| A63B 21/00 | (2006.01) |
| G09B 23/28 | (2006.01) |

(Continued)

(52) U.S. Cl.
CPC .......... *A63B 23/0238* (2013.01); *A61F 5/026* (2013.01); *A61H 1/008* (2013.01); *A61H 1/0292* (2013.01); *A63B 21/4009* (2015.10); *A63B 21/4043* (2015.10); *G09B 19/00* (2013.01); *G09B 23/28* (2013.01); *A61H 2201/165* (2013.01); *A61H 2201/168* (2013.01); *A61H 2201/1623* (2013.01); *A63B 23/0205* (2013.01); *A63B 2209/10* (2013.01); *A63B 2225/66* (2013.01)

(58) Field of Classification Search
CPC .. A61F 5/02; A61F 5/024; A61F 5/028; A61F 5/30; A63B 23/0205; A63B 23/0238; A63B 21/4009; A63B 21/4043; A63B 2209/10; A63B 2225/66; A61H 1/008; A61H 1/0292; A61H 2201/1623; A61H 2201/165; A61H 2201/168; G09B 19/00; G09B 23/28
USPC .......................................................... 602/19
See application file for complete search history.

(56) References Cited

U.S. PATENT DOCUMENTS

| 5,765,224 A * | 6/1998 | Johnson | A41C 1/02 2/44 |
| 8,449,484 B2 * | 5/2013 | Johnson | A61F 5/30 128/876 |

(Continued)

*Primary Examiner* — Keri J Nelson
(74) *Attorney, Agent, or Firm* — Duane Morris LLP; Gregory M. Lefkowitz; John E. Munro

(57) ABSTRACT

A posture training device is provided. The posture training device can include a belt with a body contacting portion having a body contact surface extending between a first edge and a second edge, an adjustable and releasable securing mechanism adapted to secure the posture training device around a midsection of a wearer. The posture training device can also include a vertebrae contact portion having a concave surface extending between a first end and a second end, and the concave surface can have a predetermined depth, such that the concave surface is configured to contact and support at least one vertebrae. A method of utilizing the posture training device to train the posture in a person is also provided.

20 Claims, 15 Drawing Sheets

(51) Int. Cl.
*A61H 1/02* (2006.01)
*A61H 1/00* (2006.01)

(56) References Cited

U.S. PATENT DOCUMENTS

2014/0135673 A1* 5/2014 Cohen .................. A61F 5/30
  602/19
2017/0143528 A1* 5/2017 Pongratz ................ A61F 5/02

\* cited by examiner

POSTURE TRAINING DEVICE AND METHOD OF USING THE SAME

CROSS-REFERENCE TO RELATED APPLICATION

The present application claims benefit of U.S. Provisional Patent Application No. 62/328,463, filed Apr. 27, 2016, the entirety is incorporated herein by reference for all purposes.

FIELD OF THE INVENTION

The present invention relates generally to a posture training device and a method of using the same.

BACKGROUND

Posture generally refers to the carriage of the body while standing or sitting down. "Proper" or "good" posture involves training the body to stand, walk, or sit in positions in which the least amount of strain is applied to the muscles and ligaments during movement. Good posture is generally associated with a healthy spine, in which the 33 vertebrae in the spinal column appear completely vertical from a rear perspective.

Strengthening the muscles that support the spine will help keep a person's back and upper body stable, and therefore help to improve the person's posture. There are several muscle groups that support the spine, including the cervical spine (neck), trapezius (neck and upper back), latissimus dorsi (side and middle back), back extensors and erector spinae (middle and lower back), quadratus lumborum (lower back), abdominals, external oblique rotators (side and lower back), internal oblique rotators (side and lower back), piriformis (buttocks), gluteus maximus (buttocks), gluteus medias (buttocks), and hamstrings (back of thigh). Obtaining and maintaining strength in those muscle groups can, among other things, help to improve one's posture, relieve back pain, and reduce the risk of injury or arthritis. In today's electronics driven society, in which people spend extended periods sitting down and looking down to view electronic devices, there is a need to help people develop and maintain good posture.

SUMMARY

In some embodiments, a posture training device is described. The posture training device can include a belt having a body contacting portion, a body contact surface extending between a first edge and a second edge, and an adjustable, releasable securing mechanism adapted to secure the posture training device around a midsection of a wearer. The posture training device can also include a vertebrae contact portion having a concave surface extending between a first end and a second end. The concave surface can have a predetermined depth, such that the concave surface is configured to contact and support at least one vertebrae.

In some embodiments, a method of training posture in a person is described. The method can include steps of providing a posture training device to the person, placing the midpoint of the posture training device behind the person's back, and coupling the first end of the belt and the second end of the belt at a front of the wearer. The method can also include a step of tightening the end portions of the belt, such that the vertebrae contact portion is pressed against at least one of the L2, L3, and L4 vertebrae of the person as a result of the tightening.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 13A is a front view of a force transfer layer as described herein, while

FIG. 15A is a front view of a vertebrae contacting portion embedded within a force transfer material as described herein, while

DETAILED DESCRIPTION

Figure 1:
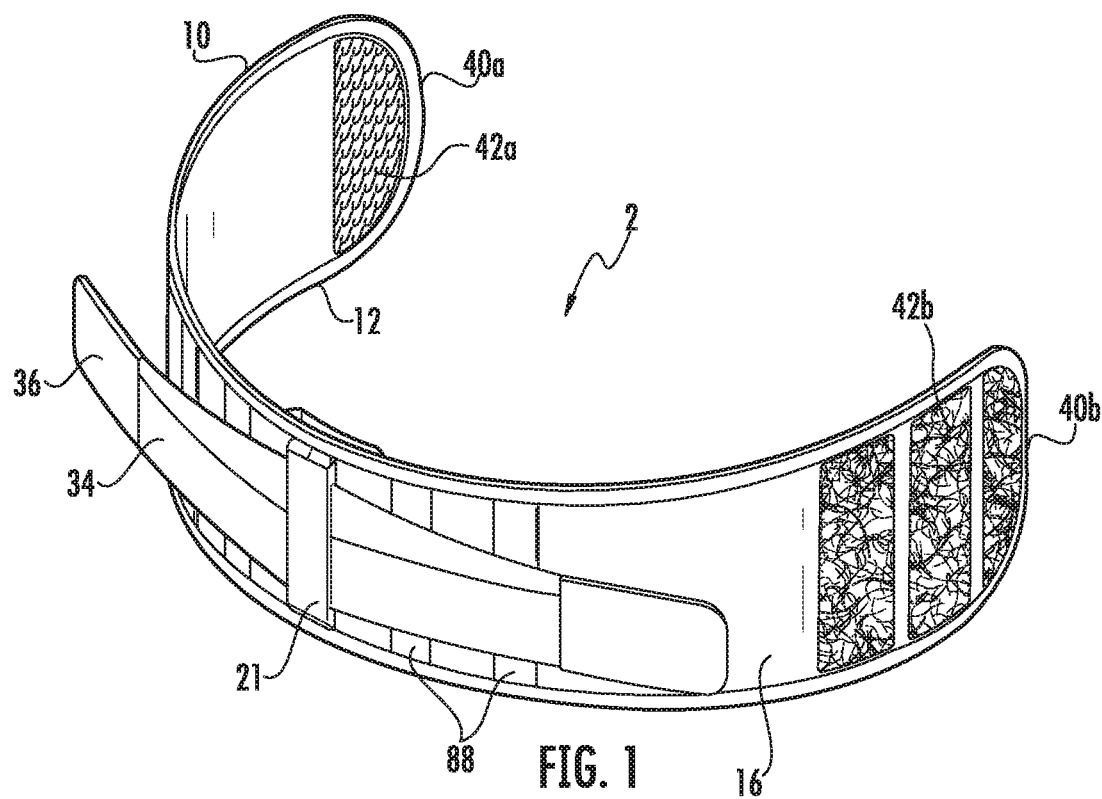
FIG. 1 is a perspective back view of a posture training device, in accordance with some embodiments.
Figure 2:
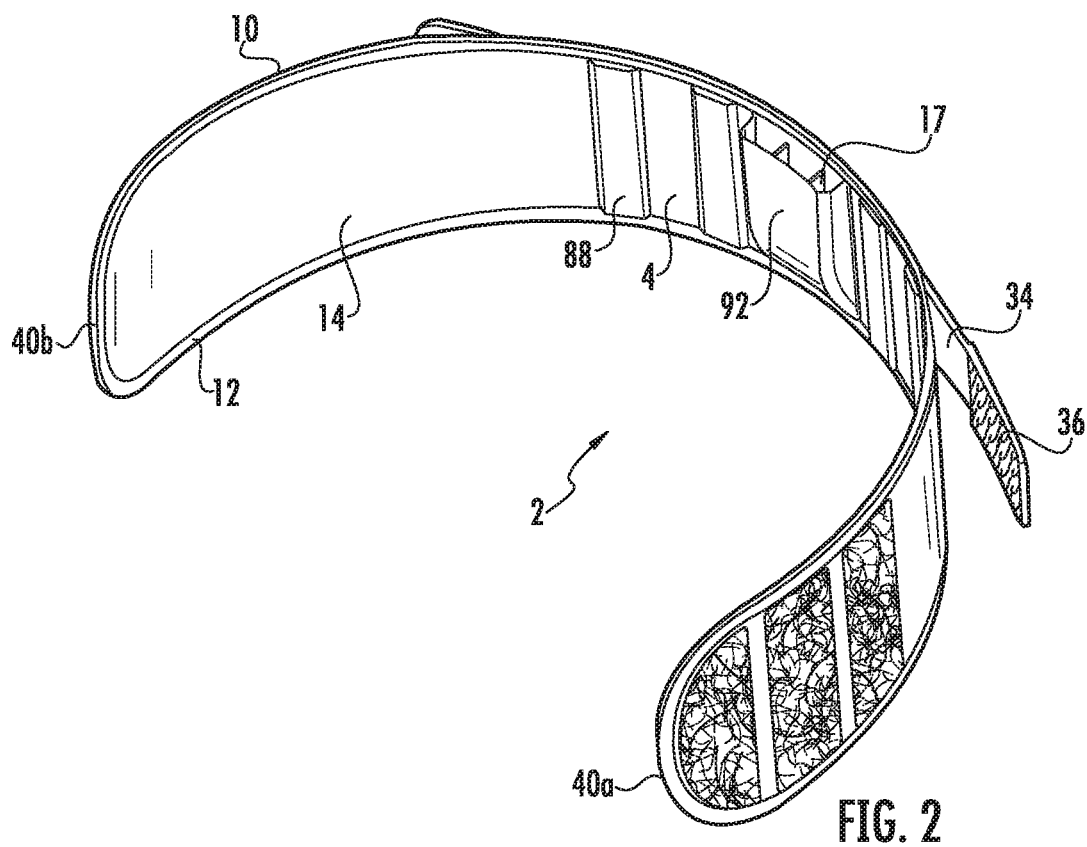
FIG. 2 is a perspective front view of a posture training device, in accordance with some embodiments.
Figure 3:
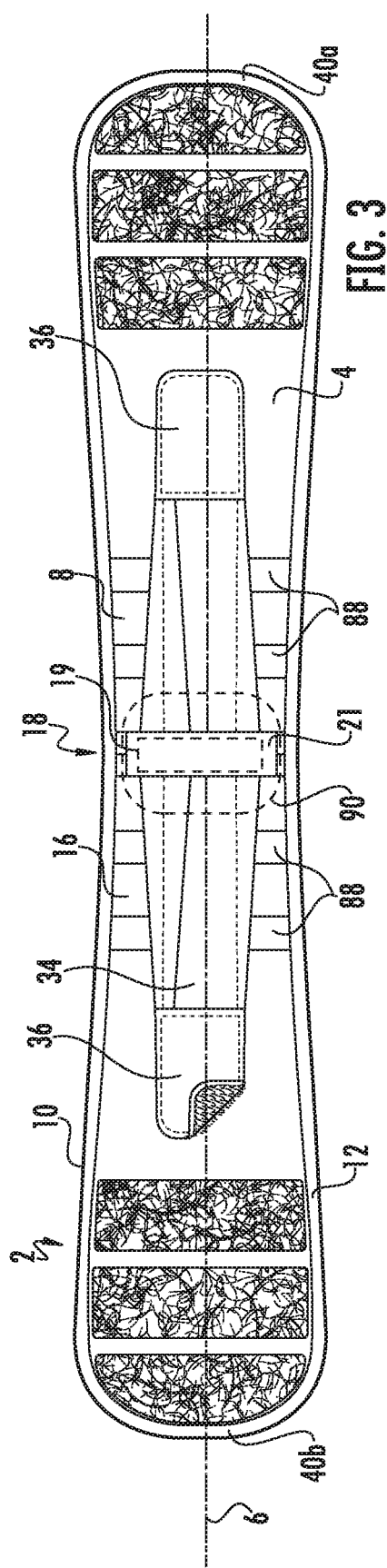
FIG. 3 is a back view of a posture training device, in accordance with some embodiments.
Figure 4:
FIG. 4 is a top view of a posture training device, in accordance with some embodiments.
Figure 5:
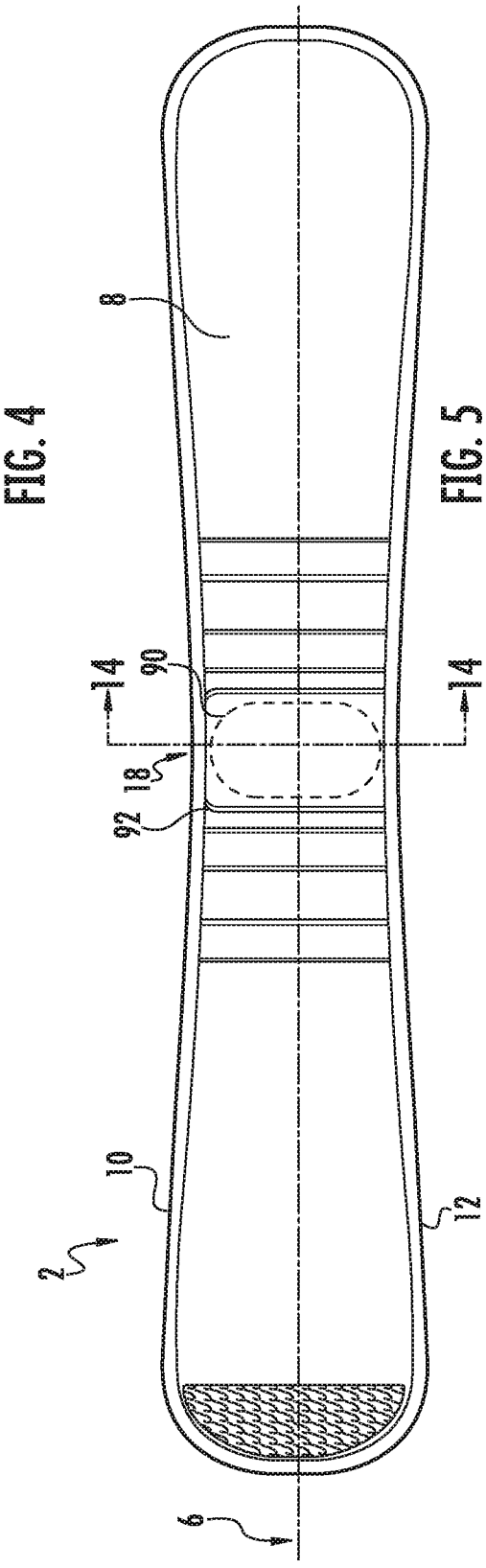
FIG. 5 is a front view of a posture training device, in accordance with some embodiments.

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise, and includes terms such as "directly" coupled, secured, etc. The term "operatively coupled" is such an attachment, coupling, or connection that allows the pertinent structures to operate as intended by virtue of that relationship.

In various embodiments, a posture training device is disclosed. The posture training device includes a longitudinal support portion extending substantially along a longitudinal axis. The longitudinal support portion can include a first and a second end for removably attaching the longitudinal support portion around a midsection of the wearer. The longitudinal support portion can include a patient contact surface extending between an upper edge and a lower edge. The longitudinal support portion can be adapted so that, when worn properly, the upper edge proximate the first and second ends exerts force proximate the xiphoid process of the wearer, while the lower edge proximate the first and second ends exerts force proximate the anterior superior iliac spine (ASIS) of the wearer.

In some embodiments, a vertebrae support is coupled to a mid-point of the longitudinal support. The vertebrae support includes a longitudinal axis of the vertebrae support extending substantially perpendicular to the longitudinal axis of the longitudinal support. The vertebrae support has a predetermined length and depth (e.g., angle of curvature) configured to contact and/or support one or more vertebrae. For example, in some embodiments, the vertebrae support is configured to contact and/or support the L3 lumbar vertebrae of a wearer. A plurality of bands, which may be elastic or inelastic, are coupled to an outer surface of the longitudinal support. The plurality of bands includes a first end and a second end. The first end and the second end are configured to releasably couple to the longitudinal support portion to maintain the vertebrae support in forceful contact with the desired vertebrae.

Figure 8:
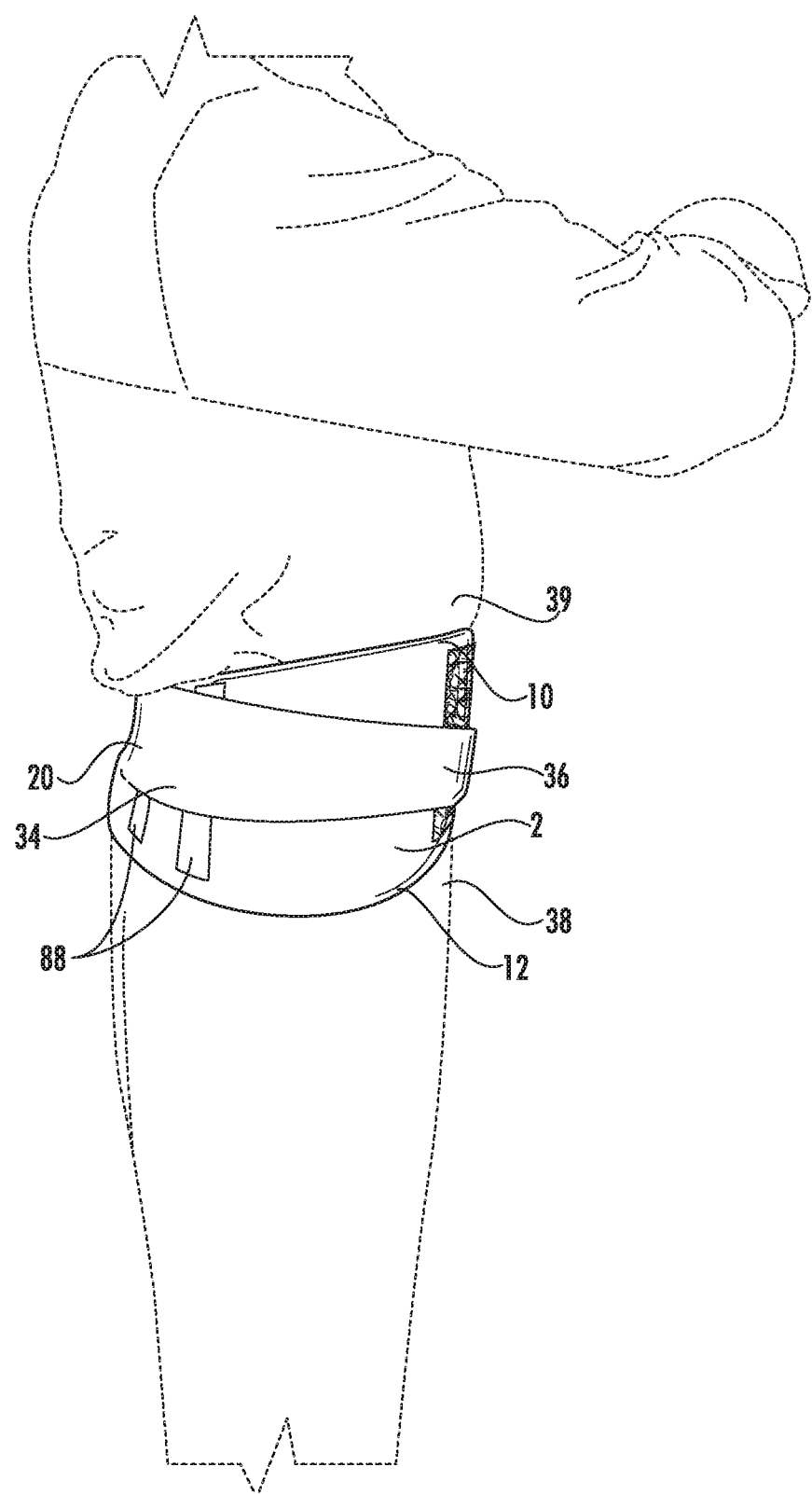
FIG. 8 is a side view of the posture training device of FIG. 1 coupled to a user, in accordance with some embodiments.
Figure 9:
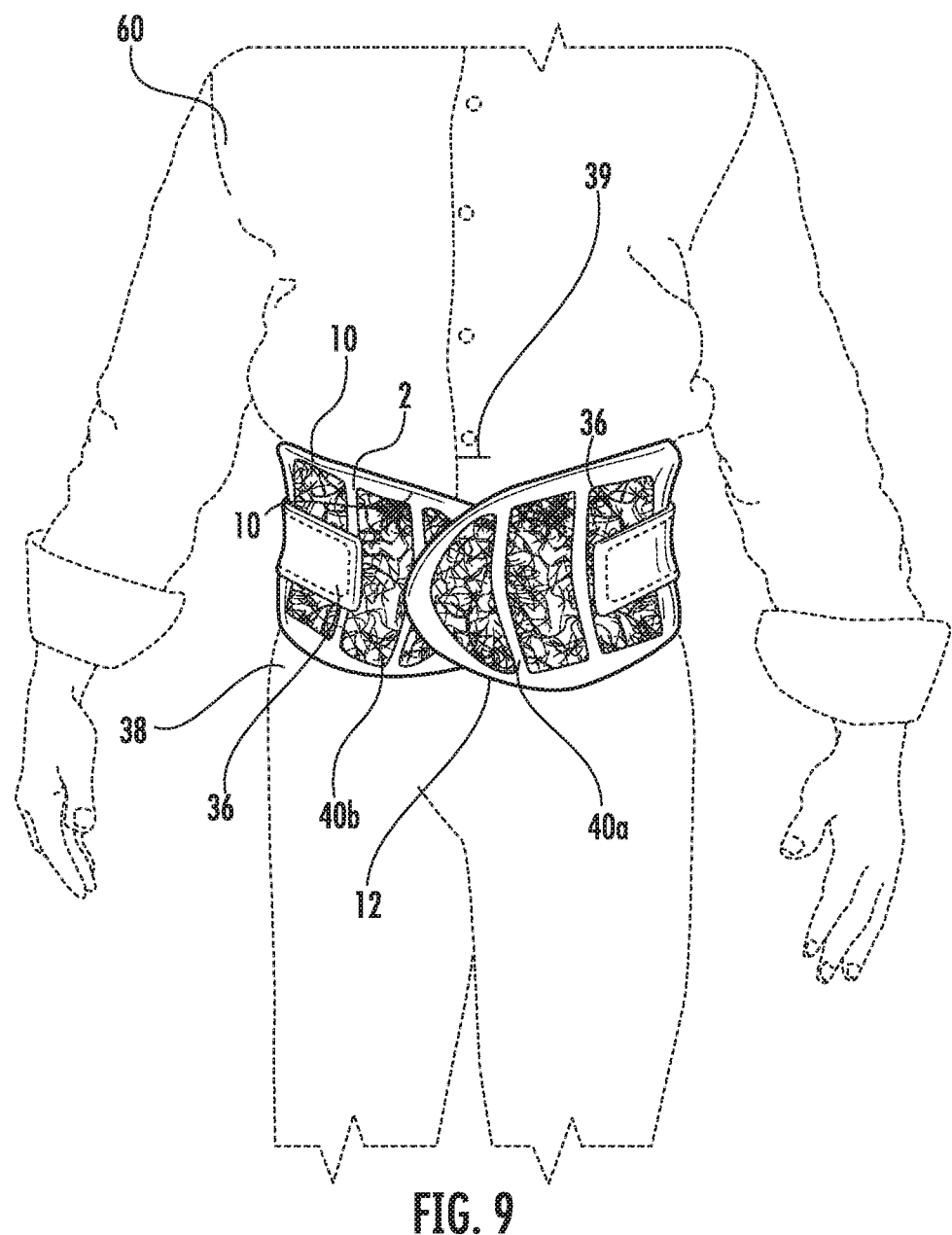
FIG. 9 is a front view of the posture training device of FIG. 1 coupled to a user, in accordance with some embodiments.
Figure 10:
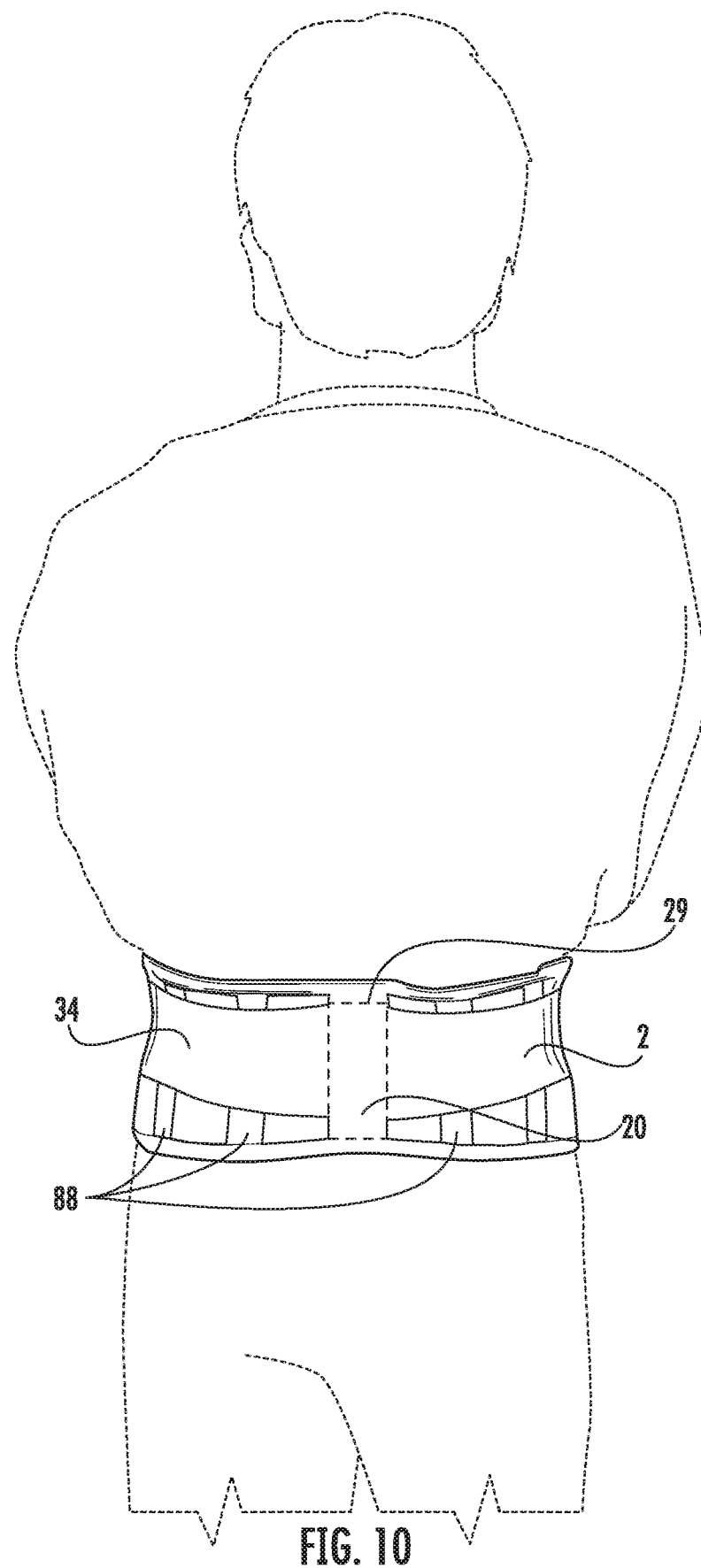
FIG. 10 is a rear view of the posture training device of FIG. 1 coupled to a user, in accordance with some embodiments.

FIGS. 1-10 and 17 illustrate one embodiment of a posture training device 2. The posture training device 2 includes a body contact portion 4 extending substantially along a longitudinal axis 6. The body contact portion 4 can be in the form of a releasably attachable belt, which can include a patient contact surface 8 extending between an upper edge 10 and a lower edge 12. The patient contact surface 8 is sized and configured to position the posture training device on a user, such as, for example, about a mid-section of a user. The patient contact surface 8 includes an inner surface 14 configured to contact a user and an opposing outer surface 16. The upper edge 10 and/or the lower edge 12 can define any suitable shape configured for placement about a midsection of a user. For example, in the illustrated embodiment, the upper edge 10 and the lower edge 12 each define a concave shape, although it will be appreciated that the upper edge 10 and/or the lower edge 12 can define a straight, convex, and/or concave shape in various embodiments. The longitudinal section 4 can be symmetrical about a midpoint 18. As shown in FIGS. 8-10, the body contact portion 4 can be adapted so that, when worn properly, the upper edge 10 proximate the first and second ends exerts force proximate the xiphoid process 39 of the wearer, while the lower edge 12 proximate the first and second ends exerts force proximate the anterior superior iliac spine 38 of the wearer.

In some embodiments, the body contacting portion 4 can include reinforcing portions 88. The reinforcing portions 88 can be aligned perpendicular to the longitudinal axis 6 in order to maintain the upper and lower edges 10, 12 of the body contacting portion 4 the proper distance from one another and prevent folding of the body contacting portion 4. In some embodiments, the reinforcing portions 88 can include a rigid and/or resilient material coupled to the body contacting portion. In some embodiments, the rigid and/or resilient material included in each reinforcing portion 88 can be a metal or polymeric strip, which can be contained within a fabric enclosure (fully enclosed, pocket, sleeve, etc.), which can be secured to the rest of the body contacting portion 4.

Figure 6:
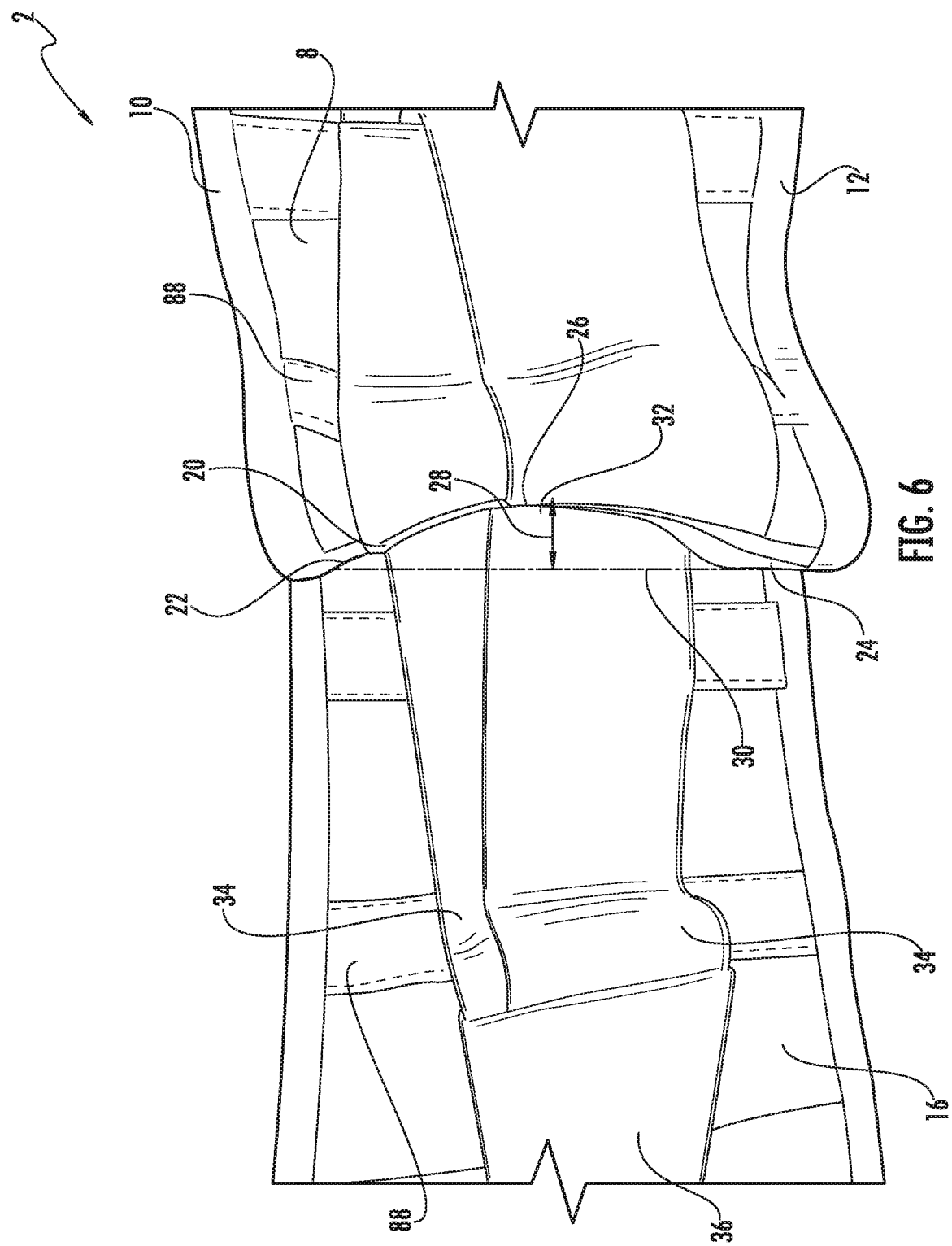
FIG. 6 is a side view illustrating a plurality of elastic straps at the back of the posture training device of FIG. 1, in accordance with some embodiments.
Figure 7:
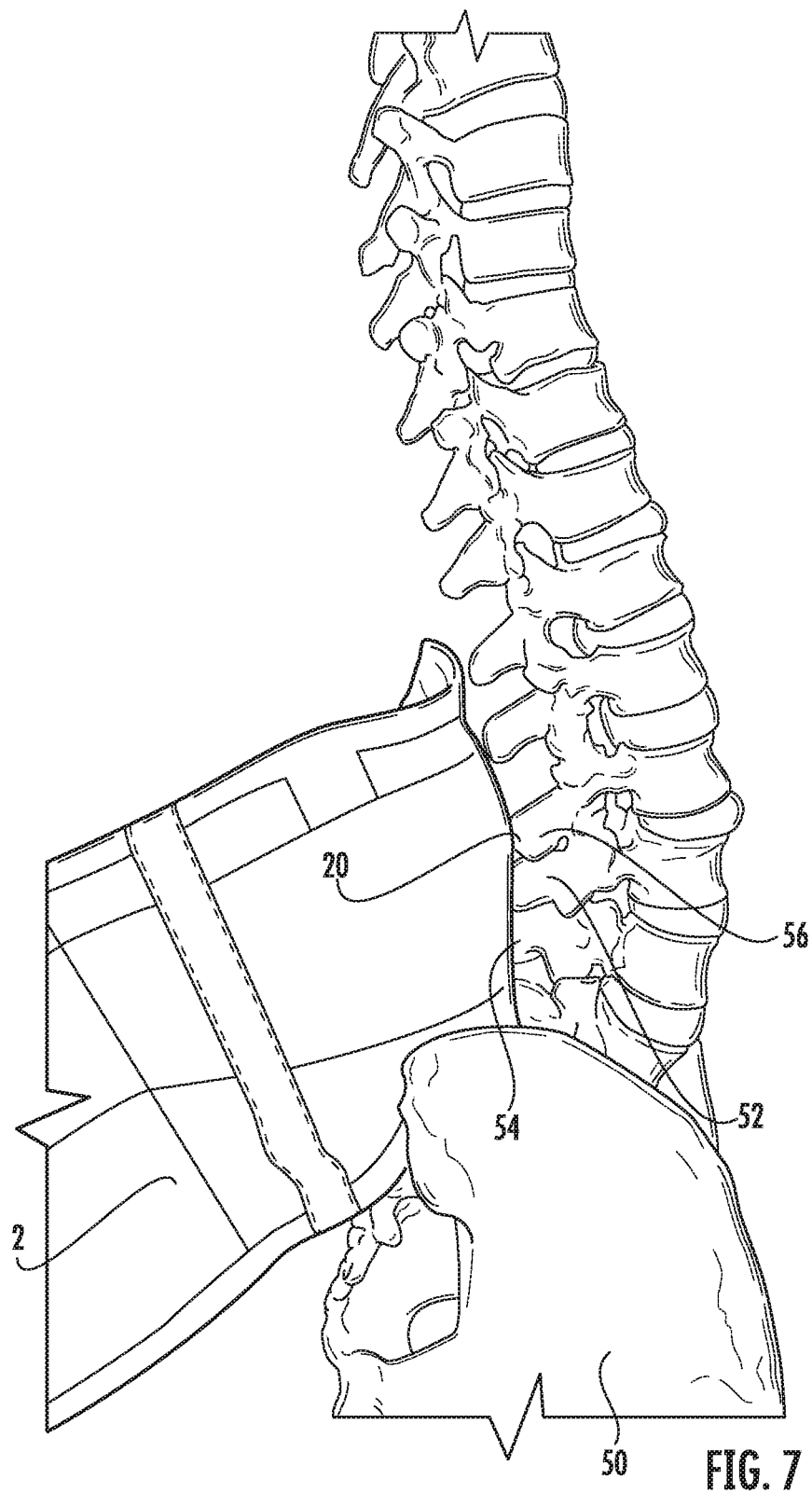
FIG. 7 illustrates an interaction between the posture training device of FIG. 1 and a spine, in accordance with some embodiments.

A vertebrae contact portion 20 is coupled the body contact portion 4. In some embodiments, the vertebrae contact portion 20 is coupled to an outer surface 16, while in other embodiments the vertebrae contact portion 20 is coupled to the inner surface 14. In some embodiments, for example in FIGS. 6-8, 10, and 17, the vertebrae contact portion 20 is coupled to a longitudinal midpoint of the body contact portion 4. In some embodiments, the vertebrae contact portion 20 is a stiff and/or resilient metal and/or polymeric strip of material and is removably secured within a pocket 19 in the posture training device 2. In some embodiments, the pocket 19 is arranged perpendicular to the longitudinal axis 6. In some embodiments, the vertebrae contact portion 20 is a stiff and/or resilient metal and/or polymeric strip of material and is removably secured within pocket 17. In some embodiments, pocket 17 is coupled to the body contact portion 4 and is within pocket 92. The vertebrae contact portion 20 includes a rigid, concave surface 26 extending between a first end 22 and a second end 24. As shown in FIGS. 6, 11C, and 12, the vertebrae contact portion 20 defines a depth 28 extending from a longitudinal axis 30 defined between the first end 22 and the second end 24 to a midpoint 32 of the rigid, concave surface 26.

In some embodiments, as shown in FIGS. 3, 5, 13-16, and 18 a force transfer layer 90 can be coupled to the posture training device 2 (e.g., body contact portion 4) such that the force transfer layer 90 is between the vertebrae contact portion 20 and the user when the posture training device 2 is worn. In some embodiments, the force transfer layer 90 can be removably coupled to the body contact portion 4 via a force transfer pocket 92. In many people with strong musculature or who carry fat deposits around the waist, the soft tissue (muscle or fat) in the back proximate the spinal cord forms an indentation. As shown in FIGS. 13A-C, the force transfer layer 90 can have a central ridge 94 adapted to fit into the soft tissue indentation. In some embodiments, the central ridge 94 can be at least twice as thick as the edges, or at least three times as thick as the edges, or at least four times as thick as edges.

Figure 14A:
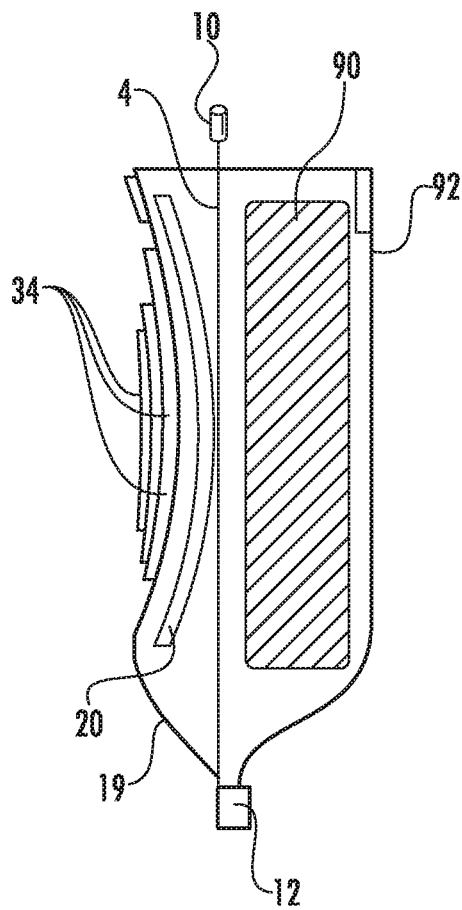
FIGS. 14A and 14B are possible cross-sectional views of the posture training device of FIG. 5 taken along cut line 14-14.
Figure 14B:
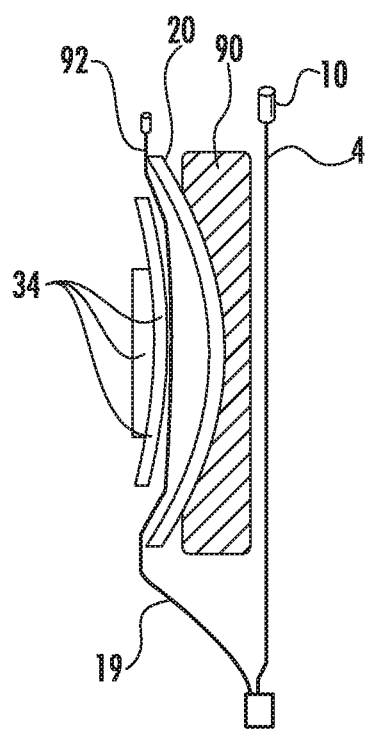
Figure 18D:
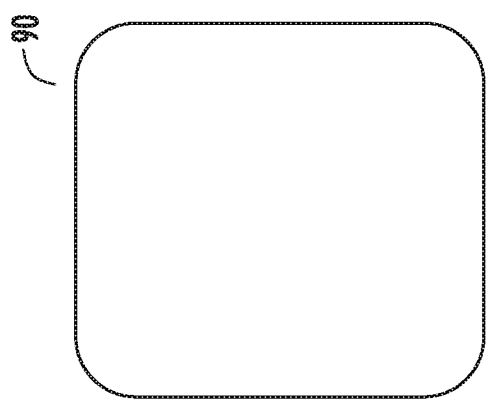
FIG. 18D is a rear view of a force transfer layer, in accordance with some embodiments.
Figure 18C:
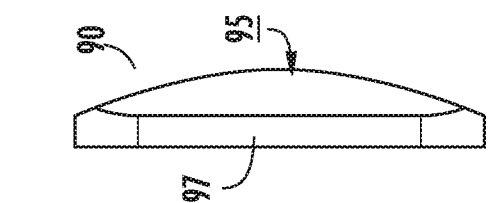
FIG. 18C is a side view of a force transfer layer, in accordance with some embodiments.
Figure 18B:
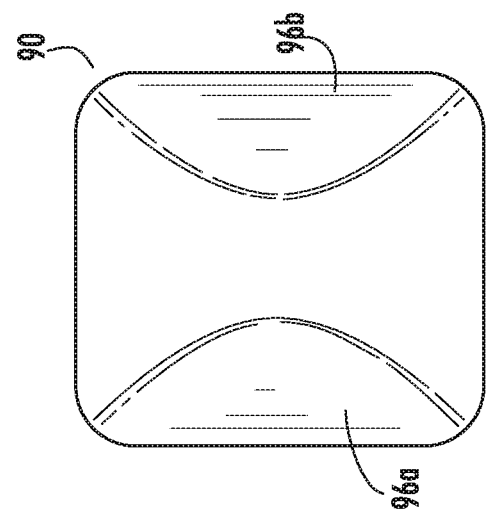
FIG. 18B is a front view of a force transfer layer, in accordance with some embodiments.
Figure 18A:
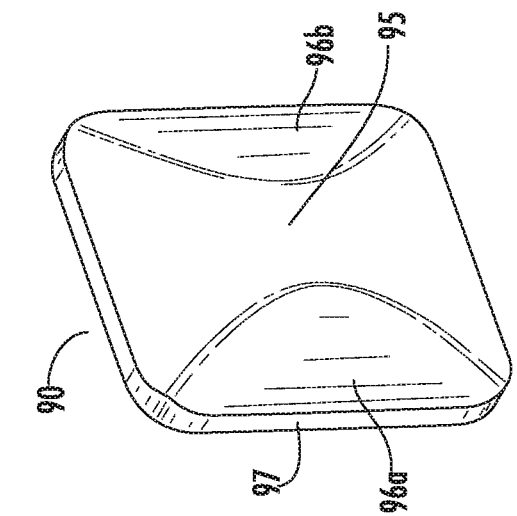
FIG. 18A is a perspective view of a force transfer layer, in accordance with some embodiments.

As shown in FIGS. 18A-D, the force transfer layer 90 can have a central ridge 95 adapted to fit into the soft tissue indentation. In some embodiments, the central ridge 95 can be at least twice as thick as the side edges 97, or at least three times as thick as the side edges 97, or at least four times as thick as the side edges 97. In some embodiments, the force transfer layer 90 can be configured with a tapered portions 96a, 96b so that the ridge 95 appears to a hyperboloid shape. In some embodiments, the force transfer layer 90 can be configured to correspond to the size and shape of vertebrae contact portion 20. For example, the curvature of the ridge 95, as shown in FIG. 18C, can correspond to the curvature of concave surface 26 or 26a in FIG. 11C. While not always necessary, the force transfer layer 90 can enhance the functionality of the posture training device 2, especially for those with pronounced indentations around the spine. A couple possible arrangements of the force transfer layer 90 are shown in FIGS. 14A-B, which are cross-sectional views of FIG. 5.

Figure 15A:
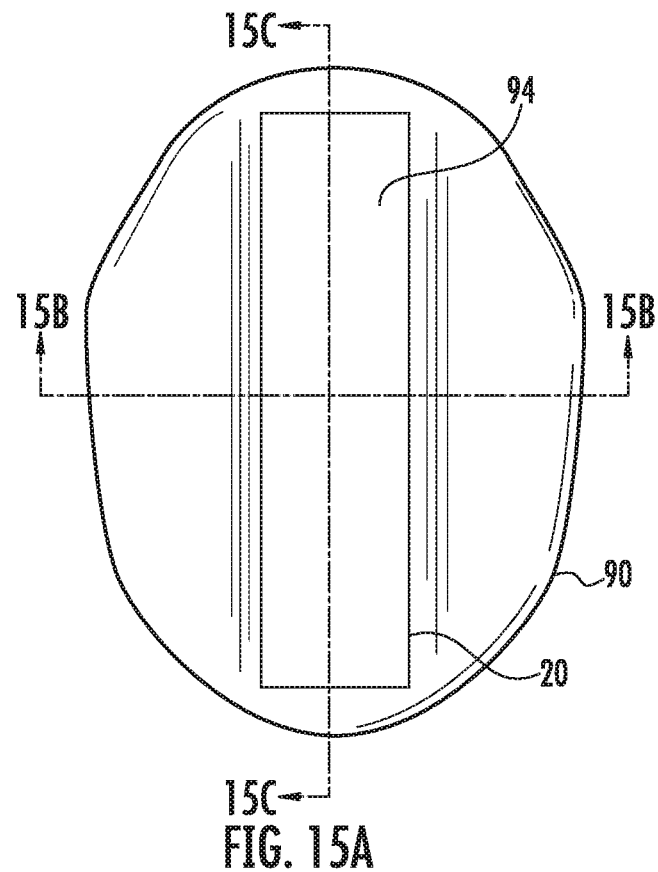
Figure 15B:
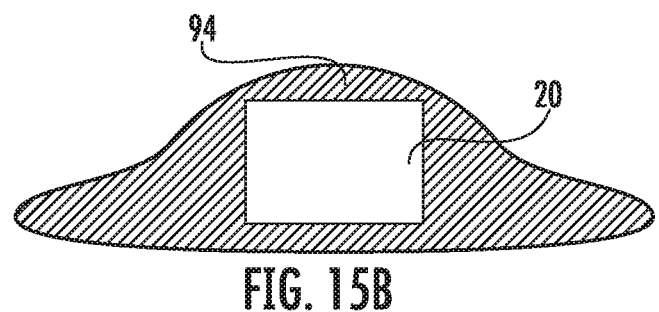
FIGS. 15B and 15C are cross-sectional views taken along cut lines B-B and C-C, respectively, of FIG. 15A.
Figure 15C:
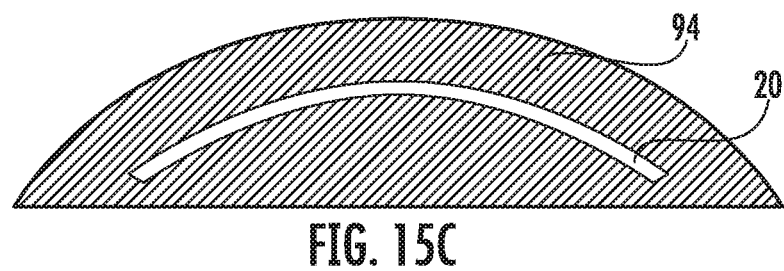
Figure 16:
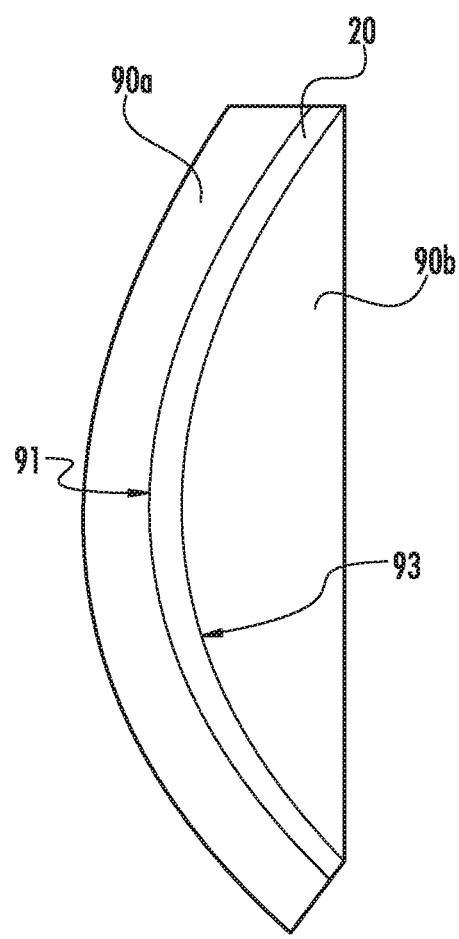
FIG. 16 is side view of a vertebrae contacting portion with force transfer materials adhered to the front and back sides thereof as described herein.
Figure 17:
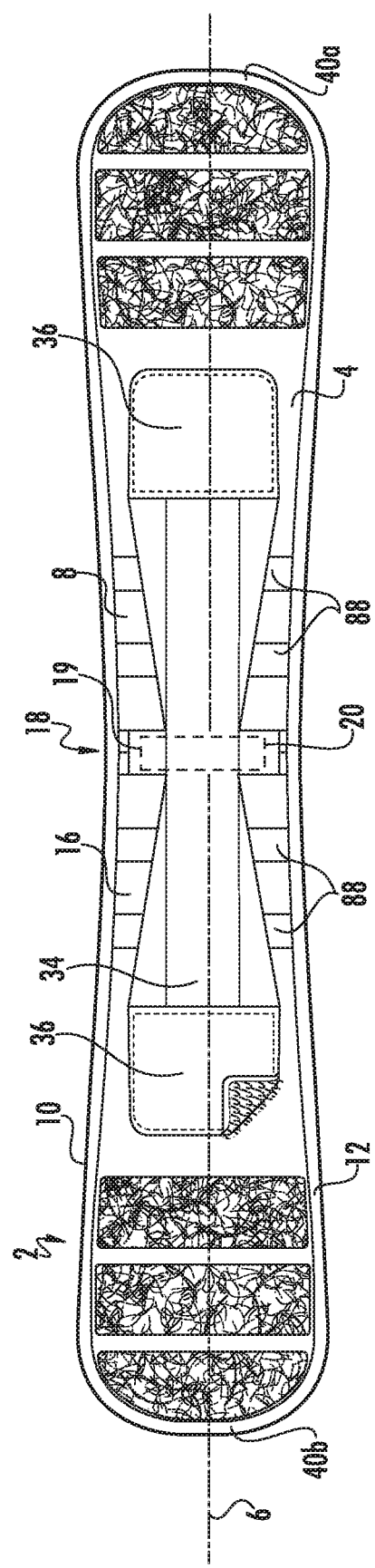
FIG. 17 is a back view of a posture training device, in accordance with some embodiments.

In some embodiments, as shown in FIGS. 15A-C, a vertebrae contacting portion 20 can be embedded in, or otherwise coupled to, the force transfer layer 90. In some embodiments, as shown in FIG. 16, the force transfer layer 90 can be adhered to a front surface 91 of the vertebrae contacting portion 20. In some embodiments, as shown in FIG. 16, the force transfer layer 90 can be adhered to a back surface 93 of the vertebrae contacting portion 20. In some embodiments, a thickness of the force transfer layer 90 at the front side of the vertebrae contacting portion 20 is at least 0.5 inches, or at least 1 inch, or at least 1.25 inches, or at least 1.5 inches, or at least 1.75 inches, or at least 2 inches. This thickness facilitates force transfer to the user regardless of the depth of any indention formed by the soft tissue surrounding the spine. In embodiments where the force transfer layer 90 and the vertebrae contacting portion 20 are coupled together, the combined device can be inserted in pocket 19 or 92.

In some embodiments, the force transfer layer 90 is also adapted to extend at least the length and width of the vertebrae contact portion 20. In some embodiments, the force transfer layer 90 is formed of a material that will distribute force from the vertebrae contact portion 20 in a more focused manner to the spine of the wearer. In some embodiments, the force transfer layer 90 can include a gel or liquid encapsulated in a polymeric material. In such embodiments, the encapsulated gel or liquid can be stored in the freezer until ready for use, which can help treat back pain, as well as, train the user on proper posture. In some embodiments, the force transfer layer 90 can be a resilient material, such as natural or synthetic rubber, silicone, polyurethane, nylon, an elastomer, and other polymers.

The vertebrae contact portion 20 has a predetermined depth, length, and width configured to align a wearer's upper body over the wearer's center of gravity when the posture training device 2 is secured properly around the wearer's midsection. For example, in some embodiments, the rigid and/or resilient concave surface 26 can have a length of between 6 and 12 cm, such as, for example, 6 cm, 7 cm, 8 cm, 8.5 cm, 9 cm, 9.5 cm, 10 cm, 11 cm, 12 cm, and/or any range selected between 6 and 12 cm. This length is measured from end-to-end along the longitudinal axis 30. In some embodiments, the rigid, concave surface 26 can have a depth 28 of about 0.5 cm to about 2 cm, such as, for example, 0.5 cm, 0.75 cm, 1 cm, 1.25 cm, 1.5 cm, 1.75 cm, 2 cm, and/or any depth 28 within any defined range between 0.5 and 2 cm. In some embodiments, the rigid concave surface 26 can have a width 29 of about 1 to about 5 cm, such as, for example, 1 cm, 2 cm 2.5 cm, 3 cm, 3.5 cm, 4 cm, 5 cm, and/or any width 29 within any range defined between 1 and 5 cm. As will be evident from FIGS. 11A-C and 12, the rigid, concave surface 26 can be defined by one or more curved and/or linear sections.

Figure 11A:
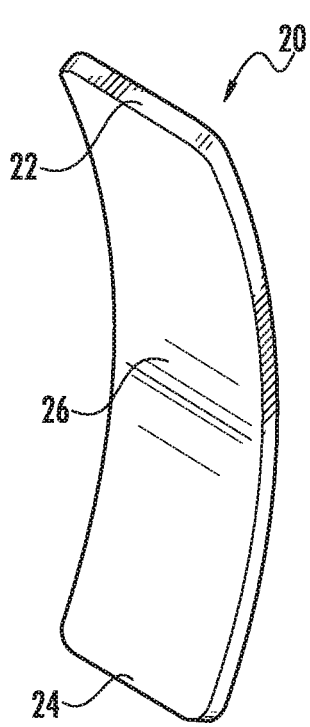
FIG. 11A is a perspective view of a vertebrae contact portion, in accordance with some embodiments.
Figure 11B:
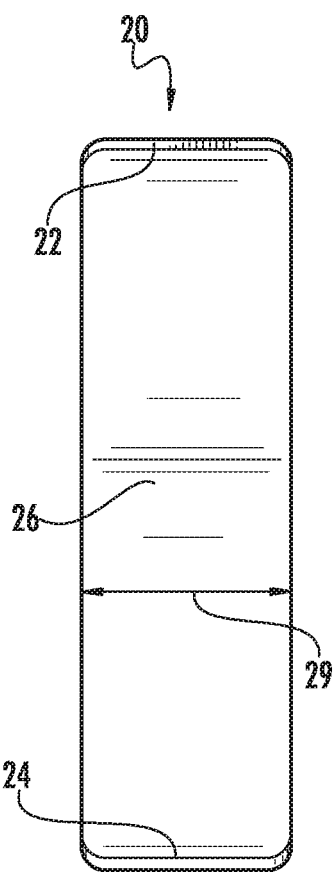
FIG. 11B is a front view of a vertebrae contact portion, in accordance with some embodiments.
Figure 11C:
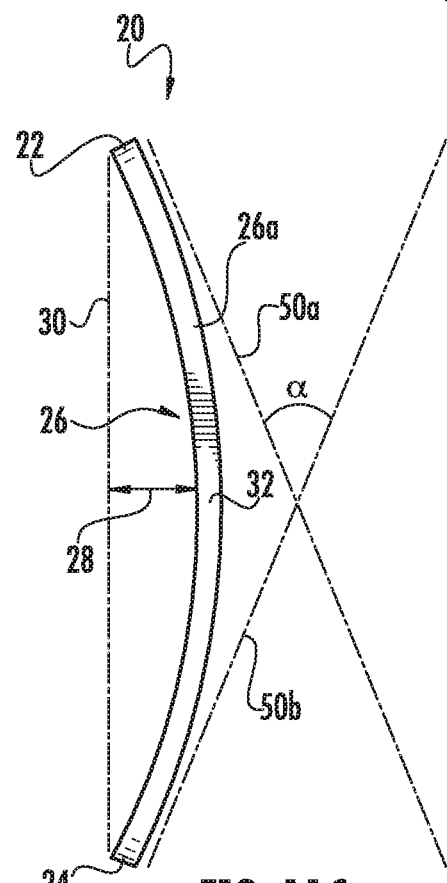
FIG. 11C is a side view of a vertebrae contact portion, in accordance with some embodiments.
Figure 12:
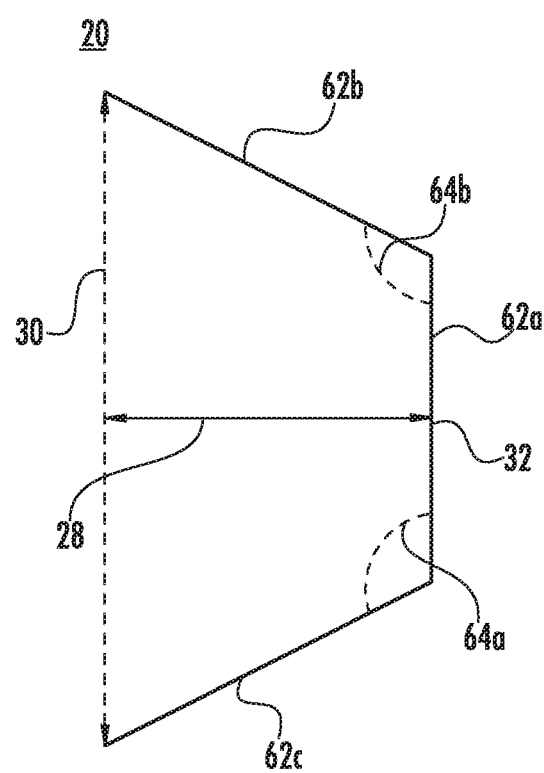
FIG. 12 illustrates vertebrae contact portion including a plurality of rigid segments defining a concave shape, in accordance with some embodiments.
Figure 13A:
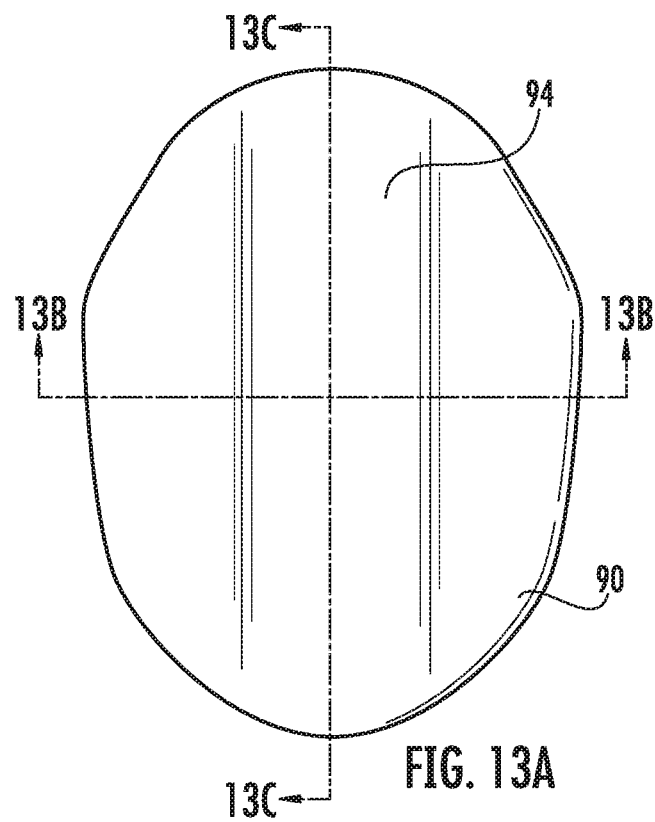
Figure 13B:
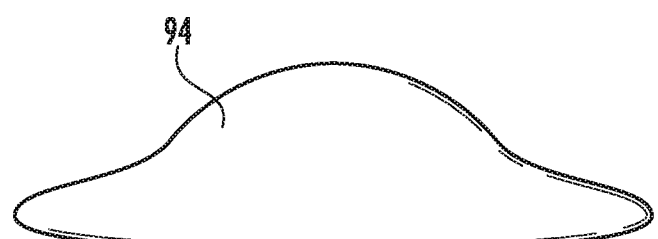
FIGS. 13B and 13C are cross-sectional views taken along cut lines B-B and C-C, respectively, of FIG. 13A.
Figure 13C:
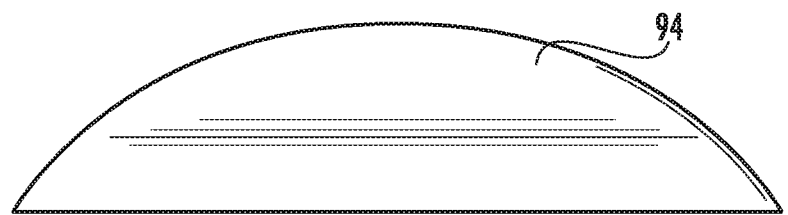

As shown in FIG. 11A-C, in some embodiments, the rigid and/or resilient concave surface 26 includes a continuously curved or semi-circular or semi-elliptical surface 26a having a radius of curvature. The concave surface 26a can be selected such that tangent lines 50a, 50b drawn from the first end 22 and the second end 24 cross at a predetermined angle (a). For example, in some embodiments, the predetermined angle can be any angle between about 30° and about 75°, such as, for example, 30°, 45°, 60°, 65°, 75°, and/or any angle selected from any range of angles between about 30° and 75°. In some embodiments, the first and second tangent lines 50a, 50b cross at a predetermined angle of about 63° (e.g., from 60-65°).

As shown in FIG. 12, in some embodiments, the rigid and/or resilient concave surface 26 includes a plurality of linear segments 62a-62c defining a concave surface 26b. The plurality of linear segments 62a-62c include a middle segment 62a having a first side segment 62b extending from a first side and a second side segment 62c extending from a second side. The first and second side segments 62b, 62c extend from the middle segment 62a at a predetermined angle 64a, 64b. In some embodiments, the predetermined angle 64a between the first side segment 62b and the middle segment 62a is equal to the predetermined angle 64b between the second side segment 62c and the middle segment 62a. For example, in some embodiments, the predetermined angle can be any angle between about 30° and about 75°, such as, for example, 30°, 45°, 60°, 65°, 75°, and/or any angle selected from any range of angles between about 30° and 75°. In some embodiments, the predetermined angle 64a, 64b is about 63°.

In some embodiments, the posture training device 2 includes a plurality of bands 34 coupled to the body contact portion 4. The bands 34 can be elastic and can include end portions 36 configured to releasably and adjustably couple to the end portions 40a, 40b of the body contact portion 4. The bands 34 can be adjusted to cause the vertebrae contact portion 20 to exert pressure at the proper location of the spine (e.g., the L2 to L4 vertebrae, but preferably at the L3 vertebrae). For example, in some embodiments, the end portions 36, 40a, 40b include a two-part fastener such as a hook-and-loop fastener, while the bands can be attached using a slidable unit, or other adjustable fasteners, in other embodiments. The bands 34 are sized and configured to extend at least partially around a wearer 60. The bands 34 maintain the vertebrae contact portion 20 in a fixed position with respect to the wearer 60. The bands 34 can be coupled to the body contact portion 4 on top of and/or beneath the vertebrae contact portion 20 in order to apply appropriate force to the spine via the vertebrae contact portion 20. A loop 21 can be coupled to the posture training device 2 such that bands 34 can be passed through the loop 21 (e.g., FIGS. 1 and 3). In some embodiments, such as that shown in FIG. 17, the plurality of bands 34 includes three bands that are parallel at a midpoint 18 and spread outwards towards end portions 36. In other embodiments, such as FIGS. 1, 3, and 6, the plurality of bands 34 includes three bands that are parallel, but spread apart, at a midpoint 18 and converge together towards end portions 36. The bands 34 can include any suitable elastic material and/or non-elastic material (e.g., nylon strapping).

The end portions 40a, 40b of the body contact portion 4 are configured to secure the posture training device 2 around the midsection of a user. In some embodiments, the end portions 40a, 40b each include portions 42a, 42b of a two-part fastener, such as a hook- and loop fastener, configured to secure the first end portion 40a to the second end portion 40b. In some embodiments, the first and second ends 40a, 40b of the body contact portion 4 are configured to contact a user 60 proximate the anterior superior iliac spine (ASIS) 38 and the xiphoid process 39 as shown in FIGS. 8-9. The posture training device 2 can be designed such that lower edge 12 proximate the end portions 40a, 40b contacts the ASIS 38 while the upper edge 10 proximate the end portions 40a, 40b contacts the xiphoid process 39. In other embodiments, the body contact portion 4 can have a greater and/or lesser width configured to contact one or more additional anatomical regions.

The end portions 36 of the bands 34 are configured to couple to the end portions 40a, 40b to apply pressure to the vertebrae contact portion 20. In some embodiments, the bands 34 are adjustable to adjust the pressure applied by the vertebrae contact portion 20 to the user.

The posture training device 2 is sized and configured to provide back support when worn by a user 60. The vertebrae contact portion 20 is sized and configured so that, when the posture training device is being worn, the vertebrae contact portion 20 applies a force to one or more vertebrae, such as, for example, an L3 lumbar. When worn, the vertebrae contact portion 20 forces the L3 lumbar into a position located over the center of gravity of the user 60. This trains the wearer about proper posture and causes engagement of one or more core stabilization muscles, such as, for example, glutes, abs, and/or any other suitable stabilization muscles.

In some embodiments, the vertebrae contact portion 20 contacts one or more additional vertebrae, such as, for example, an L2 and an L4 vertebrae. In combination with the pressure exerted to the xiphoid process and the ASIS, the pressure exerted on the L2, L3, and L4 vertebrae provides a plurality of pressure points to align the back and engage one or more core stabilization muscles, such as, for example, glutes, abs, and/or any other suitable stabilization muscles.

In another embodiment, a method of posture training is provided. The method comprises providing a posture training device 2 as provided herein and donning the posture training device 2. The donning step can include placing the midpoint 18 of the posture training device 2 behind the wearer's back, holding the end portions 40a, 40b in opposing hands and coupling the end portions 40a, 40b at a front of the wearer. The method can then include holding the end portions 36a, 36b of the straps pulling them tight and securing them to the respective end portions 40a, 40b in order to press the vertebrae contact portion 20 against at least one of the L2, L3, and L4 vertebrae. When properly donned, the upper edge 10 exerts pressure against the xiphoid process 39, the lower edge 12 exerts pressure against the ASIS 38, and the vertebrae contact portion 20 exerts pressure against the L3 vertebrae in a manner the trains the wearer to stand with the upper body over the wearer's center of gravity and maintain the position even when engaged in activities (e.g., picking up an object, sitting, walking, reaching, etc.). This causes the wearer to engage stabilization muscles, such as, the gluteal and abdominal muscles.

The method can also include wearing the posture training device 2 at least once a day for no more than 5 hours at a time for at least 2 consecutive days. In some embodiments, the posture training device 2 at least once a day for no more than 5 hours at a time for at least 3 consecutive days, or at least 4 consecutive days, or at least 5 consecutive days, or at least 6 consecutive days, or for at least 7 consecutive days. After wearing the posture training device 2 for a sufficient period of time, the wearer will learn what proper posture feels like and will strengthen the muscles necessary to achieve proper posture.

The foregoing is provided for purposes of illustrating, explaining, and describing embodiments of this invention. Modifications and adaptations to these embodiments will be apparent to those skilled in the art and may be made without departing from the scope or spirit of this invention.

What is claimed is:

1. A posture training device, comprising:
a belt having a body contacting portion having a body contact surface extending between a first edge and a second edge, wherein the belt comprises a first end and a second end adapted to be adjustably, releasably coupled together to secure the posture training device around a midsection of a wearer, the first end having a first end maximum height extending between the first edge and the second edge, and the second end having a second end maximum height extending between the first edge and the second edge; and
a vertebrae contact portion having a concave surface extending between a first end and a second end of the vertebrae contact portion, the concave surface having a predetermined depth, wherein the concave surface is configured to contact and support at least one vertebrae when secured around the midsection of the wearer, the vertebrae contact portion coupled to the body contacting portion at an intermediate location between the first end and second end of the belt, an intermediate height of the body contacting portion at the intermediate location being less than the first end maximum height and the second end maximum height; and
at least one band having a first band end adapted to adjustably, releasably couple to the first end of the belt, a second band end adapted to adjustably, releasably couple to the second end of the belt, and an intermediate portion overlapping with the vertebrae contact portion
wherein said at least one band is configured to adjust a pressure applied against the vertebrae contact portion and against the at least one vertebrae of the wearer.

2. The training device of claim 1, wherein the concave surface has a predetermined depth of at least 0.5 cm.

3. The training device of claim 1, wherein the concave surface includes a curved surface, wherein a tangent of a first end portion of the curved surface and a tangent of the second end portion of the curved surface intersect at a predetermined angle between 30° and 75°.

4. The training device of claim 1, wherein the concave surface includes a plurality of linear segments, including a middle section, a first end section coupled to a first end of the middle section, and a second end section coupled to the second end of the middle section, wherein the first end section and the second end section are coupled to the middle section at a predetermined angle between 15° and 75°.

5. The training device of claim 1, further comprising a force transfer layer coupled to the belt such that, when the belt is worn, the force transfer layer is positioned between the wearer and the vertebrae contact portion.

6. The training device of claim 5, wherein the force transfer layer is formed of a material that will distribute force from the vertebrae contact portion in a more focused manner to the spine of the wearer.

7. The training device of claim 6, wherein the force transfer layer comprises a gel or liquid encapsulated in a polymeric material.

8. The training device of claim 1, wherein the first edge of the belt contacts the wearer at approximately the xiphoid process and the second edge of the belt contacts the wearer at approximately the superior iliac spine (ASIS).

9. The training device of device of claim 1, wherein the first edge of the belt contacts the wearer at approximately the xiphoid process, the second edge of the belt contacts the wearer at approximately the superior iliac spine (ASIS), and the vertebrae contact portion contacts the wearer at approximately the L3 vertebrae.

10. The training device of claim 1, wherein the intermediate portion of the at least one band is coupled to the belt.

11. The training device of claim 1, wherein the at least one band comprises an elastic portion.

12. The training device of claim 1, wherein, when the training device is being worn, the vertebrae contact portion is positioned between the wearer and the at least one band.

13. The training device of claim 12, wherein the first band end is adapted to adjustably, releasably couple to the first end of the belt via a hook-and-loop fastener, and the second band end is adapted to adjustably, releasably couple to the second end of the belt via a hook-and-loop fastener.

14. The training device of claim 1, wherein the first band end is adapted to adjustably, releasably couple to the first end of the belt via a hook-and-loop fastener, and the second band end is adapted to adjustably, releasably couple to the second end of the belt via a hook-and-loop fastener.

15. A method of training posture in a wearer, comprising the steps of:
- providing a posture training device of claim 1 to the wearer;
- placing the midpoint of the posture training device behind the wearer's back; and
- coupling the first end of the belt and the second end of the belt at a front of the wearer.

16. The method of claim 15, further comprising:
- tightening the end portions, wherein the vertebrae contact portion is pressed against at least one of the L2, L3, and L4 vertebrae of the wearer as a result of the tightening.

17. The method of claim 15, wherein the first edge of the belt contacts the wearer at approximately the xiphoid process.

18. The method of claim 15, wherein the second edge of the belt contacts the wearer at approximately the superior iliac spine (ASIS).

19. The method of claim 15, wherein the first edge of the belt contacts the wearer at approximately the xiphoid process and the second edge of the belt contacts the wearer at approximately the superior iliac spine (ASIS).

20. The method of claim 15, wherein the first edge of the belt contacts the wearer at approximately the xiphoid process, the second edge of the belt contacts the wearer at approximately the superior iliac spine (ASIS), and the vertebrae contact portion contacts the wearer at approximately the L3 vertebrae.

* * * * *